United States Patent
Weickgenannt et al.

(10) Patent No.: US 10,329,238 B2
(45) Date of Patent: Jun. 25, 2019

(54) ISOMERIZATION OF MDACH

(71) Applicant: BASF SE, Ludwigshafen am Rhein (DE)

(72) Inventors: Andreas Weickgenannt, Mannheim (DE); Sandra Kramp, Mannheim (DE); Jan-Oliver Weidert, Schifferstadt (DE); Alexander Panchenko, Ludwigshafen (DE); Artur Kozicki, Bad Duerkheim (DE); Ralph Busch, Worms (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 15/776,603

(22) PCT Filed: Nov. 30, 2016

(86) PCT No.: PCT/EP2016/079262
§ 371 (c)(1),
(2) Date: May 16, 2018

(87) PCT Pub. No.: WO2017/093308
PCT Pub. Date: Jun. 8, 2017

(65) Prior Publication Data
US 2018/0327347 A1 Nov. 15, 2018

(30) Foreign Application Priority Data
Dec. 4, 2015 (EP) .................................. 15198049

(51) Int. Cl.
C07C 209/88 (2006.01)
C07C 211/36 (2006.01)

(52) U.S. Cl.
CPC .......... *C07C 209/88* (2013.01); *C07C 211/36* (2013.01); *C07C 2521/06* (2013.01); *C07C 2523/46* (2013.01); *C07C 2601/14* (2017.05)

(58) Field of Classification Search
None
See application file for complete search history.

(56) References Cited

U.S. PATENT DOCUMENTS

| 2012/0226017 A1 | 9/2012 | Pfeffinger et al. |
| 2016/0326094 A1 | 11/2016 | Weickgenannt et al. |

FOREIGN PATENT DOCUMENTS

| EP | 0796839 A1 | 9/1997 |
| EP | 2883863 A1 | 6/2015 |
| WO | WO 2011/032877 A1 | 3/2011 |
| WO | WO 2011/033104 A1 | 3/2011 |
| WO | WO 2016/083210 A1 | 6/2016 |

OTHER PUBLICATIONS

International Search Report dated Feb. 2, 2017, in PCT/EP2016/079262, filed Nov. 30, 2016.

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A method for isomerizing a starting mixture comprising 2,4-diamino-1-methylcyclohexane, 2,4-MDACH for short, 2,6-diamino-1-methylcyclohexane, 2,6-MDACH for short, or mixtures thereof, wherein the isomerization is carried out in the presence of a supported catalyst with zirconium dioxide as support and ruthenium as active metal.

8 Claims, No Drawings

ISOMERIZATION OF MDACH

This application is a National Stage of PCT/EP2016/079262, which was filed on Nov. 30, 2016. This application is based upon and claims the benefit of priority to European Application No. 15198049.7, which was filed on Dec. 4, 2015.

The subject matter of the present invention relates to a method for isomerizing a starting mixture comprising 2,4-diamino-1-methylcyclohexane, 2,4-MDACH for short, 2,6-diamino-1-methylcyclohexane, 2,6-MDACH for short, or mixtures thereof and is characterized in that the isomerization is carried out in the presence of a supported catalyst with zirconium dioxide as support and ruthenium as active metal.

2,4-Diamino-1-methylcyclohexane (2,4-MDACH) and 2,6-diamino-1-methylcyclohexane (2,6-MDACH) and mixtures thereof are obtainable by hydrogenation of the corresponding diaminotoluenes. EP-A 0796839 and WO 2011/033104 describe the hydrogenation of mixtures of 2,4- and 2,6-diaminotoluene.

In the hydrogenation of the diaminotoluenes, diaminomethylcyclohexanes having cis or trans isomerism are obtained. When using mixtures of 2,4- and 2,6-diaminotoluene, the result is a significant number of different cis and trans isomers.

For the further reaction of the mixtures of 2,4- and 2,6-MDACH obtained in the hydrogenation to give conversion products, it is often advantageous that the mixtures have a unique stereoisomerism. If the mixtures comprise compounds predominantly or exclusively having a cis isomerism or alternatively having a trans isomerism, this enables the production of end products having correspondingly defined stereoisomerism.

The prior European patent application with application Ser. No. 14/194,717.6 (PF 76507) describes a distillative method for separating mixtures of 2,4- and 2,6-MDACH into mixtures having predominantly cis and trans isomers.

In a distillative separation of mixtures of 2,4- and 2,6-MDACH, mixtures of compounds predominantly with the desired stereoisomerism are obtained. Naturally, mixtures are also obtained in which the compounds with the opposite undesired stereoisomerism predominate. In order to render the latter mixtures usable, or at least more usable, for the intended further reaction, the proportion having the desired stereoisomerism had to be increased in turn in these mixtures.

The object of the present invention, therefore, is a method for increasing the proportion of compounds having the desired stereoisomerism, i.e. a cis isomerism or alternatively a trans isomerism, in 2,4-MDACH, 2,6-MDACH or mixtures thereof. This method should have the highest possible selectivity and the formation of by-products should be avoided.

Accordingly, the method defined at the outset has been found.

Starting Mixture

The starting mixture comprises 2,4-MDACH, 2,6-MDACH or mixtures thereof preferably to an extent of more than 95% by weight, in particular to an extent of more than 98% by weight and particularly preferably to an extent of more than 99% by weight. In a particular embodiment, the starting mixture consists exclusively of 2,4-MDACH, 2,6-MDACH or mixtures thereof.

The starting mixture preferably comprises both 2,4-MDACH and 2,6-MDACH.

In particular, the starting mixture comprises
5 to 95% by weight 2,4-MDACH and
5 to 95% by weight 2,6-MDACH,
based on the total weight of 2,4-MDACH and 2,6-MDACH.

The starting mixture particularly preferably comprises
45 to 99% by weight 2,4-MDACH and
1 to 55% by weight 2,6-MDACH,
based on the total weight of 2,4-MDACH and 2,6-MDACH.

The starting mixture very particularly preferably comprises
70 to 95% by weight 2,4-MDACH and
5 to 30% by weight 2,6-MDACH,
based on the total weight of 2,4-MDACH and 2,6-MDACH.

The starting mixture may comprise one or more cis or trans isomers of 2,4-MDACH and 2,6-MDACH. The cis/trans isomerism refers here to the position of the two amino groups. In a cis isomer, both amino groups are above or below the plane of the ring. In a trans isomer, one amino group is above and the other below the plane of the ring.

The cis and trans isomers of 2,4-MDACH and 2,6-MDACH are listed below:

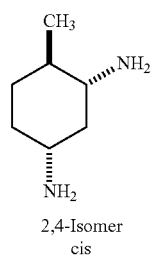

2,4-Isomer
cis

2,6-Isomer
cis

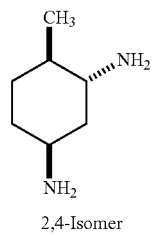

2,4-Isomer
trans

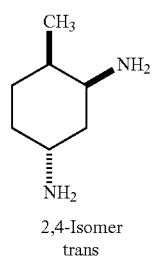

2,4-Isomer
trans

2,6-Isomer
trans

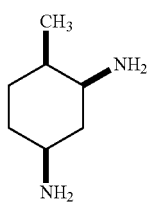

2,4-Isomer
cis

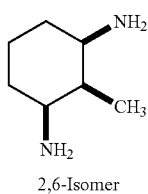

2,6-Isomer
cis

Only diastereomers are shown. Compounds 2 and 7 are meso forms. For all the other compounds, a corresponding enantiomer still exists in each case, so there are in total 12 different isomers.

As already described at the outset, 2,4-MDACH and 2,6-MDACH are typically obtained as mixtures by hydrogenation of the corresponding diaminotoluenes. From these mixtures, the compounds having the desired isomerism (cis or trans) may be separated off. A mixture remains as residue in which the compounds having the undesired isomerism (cis or trans) predominate; such a mixture is typically the starting mixture for the method of isomerization defined above.

In the following, the compounds having the undesired isomerism are in each case the total amount of all trans isomers of 2,4-MDACH and 2,6-MDACH or, alternatively, the total amount of all cis isomers of 2,4-MDACH and 2,6-MDACH 2,4-MDACH and 2,6-MDACH.

In the starting mixture, the proportion of all compounds having the undesired isomerism is generally at least 51% by weight, in particular at least 55% by weight, particularly preferably at least 60% by weight and in an especially preferred embodiment at least 70% by weight.

In the starting mixture, the proportion of all compounds having the undesired isomerism is generally at most 100% by weight, in particular at most 95% by weight, particularly preferably at most 90% by weight and in an especially preferred embodiment at most 80% by weight.

The weight data above are based on the total amount of all trans and cis isomers of 2,4-MDACH and 2,6-MDACH.

The compounds having the undesired isomerism are preferably the total amount of all trans isomers of 2,4-MDACH and 2,6-MDACH.

Catalyst

The isomerization of the starting mixture comprising 2,4-MDACH, 2,6-MDACH or mixtures thereof, is characterized in that the isomerization is carried out in the presence of a supported catalyst with zirconium dioxide as support and ruthenium as active metal.

The supported catalyst may comprise further active metals in addition to ruthenium. Suitable metals are, for example, from the groups IVb, Vb, VIb, VIIb, VIIIb, Ib or IIb of the periodic table.

These particularly include nickel, palladium, platinum, cobalt, rhodium, iridium, copper, manganese or tin.

The further active metals are preferably metals of transition group VIII of the periodic table, particularly rhodium, palladium and platinum.

The supported catalyst comprises the active metals either in elemental form or in the form of compounds, e.g. oxides. The term metal below therefore comprises elemental metals or also metals which are present in chemical bonds, be they in ionic form or covalently bound form. All weight data of the active metals however refer only to the metals as such and in the case of metal compounds do not comprise the other constituents of the compounds. When using the active metals in the form of their oxides or optionally also other compounds, reduction of the oxides to the metals generally takes place at elevated temperatures, particularly in the presence of hydrogen. This reduction may take place at the start of the reaction or can be carried out beforehand in a separate step.

In a preferred embodiment, at least 30% by weight, in particular at least 50% by weight, particularly preferably at least 70% by weight and especially preferably 90% by weight of the active metals of the supported catalyst is ruthenium. In a particular embodiment, the supported catalyst exclusively comprises ruthenium as the active metal.

The supported catalyst comprises active metals, or exclusively ruthenium in the particularly preferred embodiment, preferably in a total amount of 0.01 to 20 percent by weight, preferably 0.05 to 15 percent by weight, particularly preferably 0.1 to 10 percent by weight, based on the total weight of the supported catalyst.

The preparation of the supported catalyst is known.

The zirconium dioxide support may be present for example in the form of extrudates, spheres or tablets, for example, with diameters of 1-10 mm, or preferably as a powder. The active metals can be applied to the support in the form of metal salt solutions for example. The support can be made into a desired form before or after application of the active metals.

The supported catalyst is preferably dried at temperatures of up to 300° C. and subsequently calcined at temperatures up to 700° C. or calcined directly at up to 700° C.

The supported catalyst is preferably activated with hydrogen at a temperature of, for example, 100-350° C. before use. This may be accomplished after introducing the catalyst into the reactor, for example, before or after starting the isomerization.

The supported catalyst is often activated before introduction into the reactor and then passivated on the surface with oxygen, so that it may still be stored or is safe to handle. Only in the reactor does the subsequent activation by e.g. hydrogen then take place.

The Method

The isomerization may be carried out in the liquid phase or gas phase. In the case of a liquid phase isomerization, the temperature and pressure are selected so that the starting mixture is liquid during the isomerization.

The isomerization is preferably carried out in the liquid phase.

The isomerization is preferably carried out at a temperature of 20 to 300° C., preferably 50 to 200° C., especially 80 to 200° C. This temperature corresponds to the temperature of the starting mixture during the isomerization.

In a particularly preferred embodiment, the temperature is at most 180° C.

A particularly preferred temperature range is therefore 120 to 180° C. or 140 to 180° C.

The isomerization may be carried out at reduced pressure, standard pressure or positive pressure. In general the pressure is 0 to 500 bar. In particular, the pressure may be, for example, 20 to 300 bar. A desired pressure may be set by feeding in appropriate amounts of hydrogen or inert gas. Hydrogen is typically used to activate the catalyst and may therefore at the same time serve to set an appropriate pressure.

In reactions in the liquid phase, the pressure selected generally has little influence on the outcome of the reaction.

Solvents may also be used in the isomerization, preferably those which are miscible with the starting mixture. Preferably, no solvents are used.

The isomerization may be carried out continuously or discontinuously (batch method).

In the batchwise procedure, the isomerization may be carried out, for example, in a stirred tank or stirred autoclave, a loop reactor, a jet loop reactor, a bubble column or a fixed bed reactor with pumping circuit. The batchwise isomerization is preferably carried out in a stirred tank or a stirred autoclave. In the batchwise procedure, the starting mixture and the catalyst are generally initially charged entirely in the reactor.

In the batchwise procedure, the catalyst may be introduced into the reactor, for example, as a fixed bed or in another form. In a preferred embodiment, the catalyst may be suspended in the starting mixture and the resulting suspension is filled into the reactor.

In the continuous procedure, the hydrogenation is carried out, for example, in a continuously operating stirred tank reactor, a continuously operating loop reactor, a continuously operating jet loop reactor, a continuously operating bubble column or a continuously operating fixed bed reactor with pumping circuit or a stirred tank cascade. In the continuous procedure, the starting mixture or solution thereof is fed in continuously and the resulting isomerized mixture (product mixture) is discharged. In the continuous procedure, the catalyst is located in the reactor, for example as a fixed bed and is only renewed and/or regenerated as required.

The product mixture obtained can be further processed.

The catalyst can be separated from the product mixture, for example by a solid-liquid separation such as filtration, sedimentation or centrifugation.

The product mixture obtained comprises cis and trans isomers. The proportion of previously predominant undesired isomers is reduced and the proportion of the desired isomers is increased. An increase of the proportion of desired isomers cannot be achieved beyond the thermodynamic equilibrium. The thermodynamic equilibrium of the cis to trans isomers of 2,4-MDACH and 2,6-MDACH is generally around 60:40.

The product mixture is therefore preferably separated by distillation into a cis-rich and a trans-rich fraction. The fraction having the undesired isomerism can be fed back again into the isomerization process.

The method described above achieves an effective isomerization of the undesired isomers to the desired isomers. In catalytic reactions of 2,4-MDACH and 2,6-MDACH, monoamines such as methylcyclohexylamines (MCHA for short) can be readily formed by elimination of ammonia. In the catalytic method described above, only very little MCHA is formed. The method therefore has high selectivity with respect to 2,4-MDACH, 2,6-MDACH or mixtures thereof.

EXAMPLES

Various catalysts were tested in the method of isomerization of MDACH and, at the end of the isomerization, the isomer distribution and the selectivity were measured. The proportion of cis and trans MDACH in the MDACH starting mixture, the reaction conditions, the selectivity and the ratio of cis to trans MDACH at the end of the isomerization are reported in Table 1.

The isomer ratio and the selectivity were determined in this case by gas chromatography by measuring the areas after assigning the signals to the individual isomers.

Cis- or trans-enriched MDACH starting mixtures were initially charged in an autoclave and the amount of catalyst specified was added. Subsequently, the autoclave was tightly sealed and flushed with hydrogen. After adjusting the temperature according to Table 1, the system was pressurized (with hydrogen) according to Table 1 and the reaction mixture was stirred for the time specified. At the end of the reaction time, the autoclave was vented to room pressure and cooled to room temperature.

The composition of the starting mixtures and the end products were investigated by gas chromatography (GC). For this purpose, the mixture is dissolved in dioxane. This solution is injected into the gas chromatograph with the aid of a syringe. The gas chromatograph is equipped with a 30 m long column having an internal diameter of 0.25 mm and a film thickness of 0.5 μm. The column itself comprises as stationary phase 35% by weight diphenyl- and 65% by weight dimethylpolysiloxane (RTX35 Amine column from Resteck Corporation). Helium is used as carrier gas or mobile phase. The helium flow rate is adjusted to 40 ml/min so that a split ratio set to 40:1 gives constant flow of 1 mL/min helium through the column. To determine the substances to be investigated, the gas chromatograph has a flame ionization detector which is operated at 280° C. The column in the gas chromatograph is operated at a temperature in the range of 100 to 250° C.

In order to be able to determine the percentages by weight of the peaks to be determined, a defined amount of a standard (dodecane) is added to the mixture dissolved in dioxane. The mixture thus obtained is injected onto the column at an injection temperature of 100° C. and an inlet pressure of 1 bar. A heating rate of 1° C./min is initially set which is maintained until a column temperature of 120° C. is reached. As soon as this temperature is reached, the column heating rate is readjusted to 5° C./min and maintained up to a final temperature of 250° C. The column temperature is then maintained at 250° C. for 10 minutes.

Catalysts Used

Catalyst 1:
  13% by weight Ni, 13% by weight Co, 20% by weight Cu and 54% by weight $Al_2O_3$ (support)

Catalyst 2
  50% by weight Ni and 50% by weight $ZrO_2$

Catalyst 3
  5% by weight Ru and 95% by weight $ZrO_2$

| Catalyst | Amount [%] | Pressure [bar] | Temperature [° C.] | Time [h] | Selectivity [%] | Ratio cis:trans in the starting mixture | Ratio cis:trans in the product mixture |
|---|---|---|---|---|---|---|---|
| 1 | 1 | 100 | 160 | 12 | 96 | 75:25 | 66:34 |
| 2 | 1 | 100 | 160 | 12 | 95 | 75:25 | 65:35 |
| 3 | 1 | 100 | 160 | 12 | 99.7 | 75:25 | 65:35 |
| 3 | 1 | 100 | 160 | 12 | 99 | 20:80 | 64:36 |
| 3 | 1 | 100 | 160 | 12 | 99 | 100:0 | 55:45 |

Example 2

8 mL of the ruthenium supported catalyst according to the invention (5% by weight Ru on $ZrO_2$) were filled into a tubular reactor heated with an external jacket (5 m height, 2 mm internal diameter). The reactor is then firstly flushed with hydrogen and subsequently fed with cis-enriched MDACH. It was isomerized at varying temperature and hydrogen pressure, wherein the catalyst hourly space velocity was 1 kg MDACH/kg cat*h, and the reactor was operated with recirculation, i.e. a portion of the output is recycled into the reactor. The reaction outputs were analyzed by gas chromatography and the isomer distribution was determined.

| Run time [h] | Temperature [° C.] | Pressure [bar] | Ratio cis-trans | Selectivity [%] |
|---|---|---|---|---|
| Reactant | — | — | 99:1 | — |
| 24 | 130 | 150 | 89:11 | 99 |
| 72 | 150 | 150 | 71:28 | 99 |
| 96 | 160 | 150 | 65:35 | 99 |
| 121 | 150 | 50 | 72:28 | 99 |
| 146 | 150 | 100 | 72:28 | 99 |
| 171 | 150 | 150 | 71:29 | 99 |
| 384 | 150 | 150 | 71:29 | 99 |
| 432 | 155 | 150 | 69:31 | 99 |

The invention claimed is:

1. An isomerization method, comprising:
   hydrogenating a composition comprising at least one of 2,4-diaminotoluene and 2,6-diaminotoluene, to obtain a starting mixture comprising at least one of 2,4-diamino-1-methylcyclohexane and 2,6-diamino-1-methylcyclohexane;
   separating the starting mixture to obtain a cis-enriched or trans-enriched mixture comprising at least one of the 2,4-diamino-1-methylcyclohexane and the 2,6-diamino-1-methylcyclohexane; and
   isomerizing the cis-enriched or trans-enriched mixture in the presence of a supported catalyst with zirconium dioxide as support and ruthenium as active metal, to obtain a product mixture,
   wherein the isomerizing is a cis/trans isomerization that alters the cis/trans ratio of the product mixture relative to the cis-enriched or trans-enriched mixture.

2. The method according to claim 1, wherein the cis-enriched or trans-enriched mixture comprises at least one of the 2,4-diamino-1-methylcyclohexane and the 2,6-diamino-1-methylcyclohexane in a content of more than 95% by weight.

3. The method according to claim 1, wherein the cis-enriched or trans-enriched mixture comprises 5 to 95% by weight of the 2,4-diamino-1-methylcyclohexane and 5 to 95% by weight of the 2,6-diamino-1-methylcyclohexane, based on a total weight of the 2,4-diamino-1-methylcyclohexane and the 2,6-diamino-1-methylcyclohexane.

4. The method according to claim 1, wherein the isomerization is carried out at a temperature of 80 to 200° C.

5. The method according to claim 1, wherein the isomerization is carried out continuously.

6. The method according to claim 1, wherein the isomerizing occurs in the presence of hydrogen.

7. The method according to claim 1, wherein the isomerizing alters the cis/trans ratio by increasing the proportion of trans isomers in the product mixture relative to the proportion of trans isomers in the cis-enriched or trans-enriched mixture.

8. The method according to claim 1, wherein the isomerizing alters the cis/trans ratio by increasing the proportion of cis isomers in the product mixture relative to the proportion of trans isomers in the cis-enriched or trans-enriched mixture.

* * * * *